United States Patent
Parab et al.

[11] Patent Number: 5,807,600
[45] Date of Patent: Sep. 15, 1998

[54] REDUCTION OF CUTANEOUS ATROPHY

[75] Inventors: Prakash Parab, Williamsville, N.Y.; Robert Lavker, Malvern; James Leyden, Haverford, both of Pa.

[73] Assignee: Bristol-Myers Squibb Company, New York, N.Y.

[21] Appl. No.: 481,943

[22] Filed: Jun. 7, 1995

Related U.S. Application Data

[63] Continuation of Ser. No. 272,465, Jul. 11, 1994, abandoned, which is a continuation of Ser. No. 671,577, Mar. 19, 1991, abandoned.

[51] Int. Cl.$^6$ .......................... A61K 7/00; A61K 31/185
[52] U.S. Cl. .......................... 424/401; 514/557; 514/553; 514/861; 514/863; 514/864
[58] Field of Search .......................... 424/401; 514/557, 514/553, 861, 863, 864, 169

[56] References Cited

U.S. PATENT DOCUMENTS 5,254,343  10/1993  Parah .................................... 424/401

FOREIGN PATENT DOCUMENTS 0415766  8/1989  European Pat. Off. .
0413528  2/1991  European Pat. Off. .

OTHER PUBLICATIONS

Merck Manual 1987, p. 2248.

*Primary Examiner*—Gollamudi S. Kishore
*Attorney, Agent, or Firm*—Morton S. Simon

[57] ABSTRACT

The cutaneous atrophy associated with the use of steroids topically can be ameliorated using salts of certain α-hydroxyacids.

20 Claims, 2 Drawing Sheets

1 …

REDUCTION OF CUTANEOUS ATROPHY

This application is a continuation of application Ser. No. 08/272,465, filed Jul. 11, 1994, now abn., which is a continuation of application Ser. No. 07/671,577 filed Mar. 19, 1991 now abn.

BACKGROUND

The use of topical steroids is known to result in certain unwanted side effects, among them cutaneous atrophy, or diminution of the epidermis and dermis, at or near the cite of steroid application. Such atrophy is generally characterized by thinning, shininess, increased transparency and telangiectasia.

There are many regimens and a variety of reasons for treating conditions with steroids and/or hydroxyacid-based reagents. Applicants know of no references to the use of hydroxyacid salts, e.g. lactates, to ameliorate the adverse effects of topical steroid usage. U.S. Pat. No. 4,105,783 describes the treatment of dry skin, or "ichthyosis", using the acid, amide or ammonium salt of an $\alpha$- or $\beta$-hydroxyacid. Lactic acid, or $\alpha$-hydroxypropionic acid, is one of the $\alpha$-hydroxyacids mentioned.

U.S. Pat. No. 4,246,261 shows topical compositions containing steroids in which the efficacy of the steroid used is enhanced via the use of salts of lactic or other $\alpha$-hydroxyacids, derived using various bases.

U.S. Pat. No. 4,363,815 deals with compositions for treating skin inflammation or disturbed keratinization. Hydroxyacid/base reaction products are disclosed as useful therein.

U.S. Pat. No. 4,485,091 refers to skin creams which contain sodium and potassium lactates as buffers.

E.P.O. Publication 0273202 discloses combinations of therapeutic agents with hydroxycarboxylic acids or salts thereof. At page 16, an ointment containing betamethasone dipropionate and 2-methyl-lactic acid is recited.

Lac-Hydrin® lotion, a product of Westwood Squibb Pharmaceuticals, Inc. (Buffalo, N.Y.), is described on page 2285 of the 1990 *Physician's Desk Reference* as 12% lactic acid, neutralized with ammonium hydroxide (i.e., ammonium lactate). The lotion has a pH of 4.5–5.5 and is disclosed as useful in treating dry, scaly skin (xerosis), ichthyosis vulgaris and the itching associated with these conditions.

THE INVENTION

It has been discovered that certain salts of alpha-hydroxyacids thicken the skin, specifically the viable epidermis, and increase certain dermal components (ground substance) so that the atrophic effects of topical steroid usage are lessened.

In a preferred embodiment, a 0.05% clobetasol 17-propionate cream was applied to the skin of a group of subjects every morning for four weeks. Buffered ammonium lactate (12% Lac-Hydrin®) was applied eight hours after each steroid application. Other groups received applications of only steroid or ammonium lactate salt once daily.

Skin treated with only steroid showed a 51% decrease in thickness, while that treated with steroid followed by ammonium lactate showed only a 35% decrease in thickness.

OBJECTS OF THE INVENTION

It is one object of the invention to provide compositions and processes for treating skin atrophy.

It is another object to provide compositions and processes for thickening skin.

It is yet another object of the invention to increase the ground substance in the viable epidermis of subjects and, thereby, ameliorate the effects of biological aging and/or damage by chemical agents or light.

The compositions and the processes of the invention employ useful quantities of salts of certain $\alpha$-hydroxyacids. Optionally, they may also employ one or more steroid components.

ADVANTAGES

The compositions and methods of the invention have several advantages over other dermatological systems now in use.

One principal advantage is the lessening of the cutaneous atrophy usually associated with the topical use of steroids and some other medicaments.

Another is the fact that, while lessening one or more of the side effects of such drugs as steroids, the salts of the invention do not alter the efficacy of these drugs in any way. Accordingly, there is no "masking" or "dilution" of the steroid used.

Still another advantage is the compatibility of the salts of the invention with steroids and other topical therapeutic agents. The salts may be simply blended into formulations containing the steroid.

Thus, the salts of the invention may be administered either along with a steroid or other topical drug or in a separate step, that is, either concomitant therewith, previous thereto or subsequent thereto. It has been found that using the salt after use of the steroid can lessen the atrophic effects of the steroid without altering its beneficial effects.

The salts of the invention can also be used in any system in which temporary thickening of the epidermis is desired. For example, persons with known sensitivities to certain agents, e.g. sunlight or certain hair or makeup preparations, and those whose skin has become biologically aged can have their skin toughened or made less sensitive by using the systems of the invention before exposing their skin to harmful agent(s).

These and other advantages of the invention will be apparent after a consideration of the following description and claims.

1*a*. Control

1*b*. 12% ammonium lactate treatment

1*c*. clobetasol propionate treatment

Figure 1A:
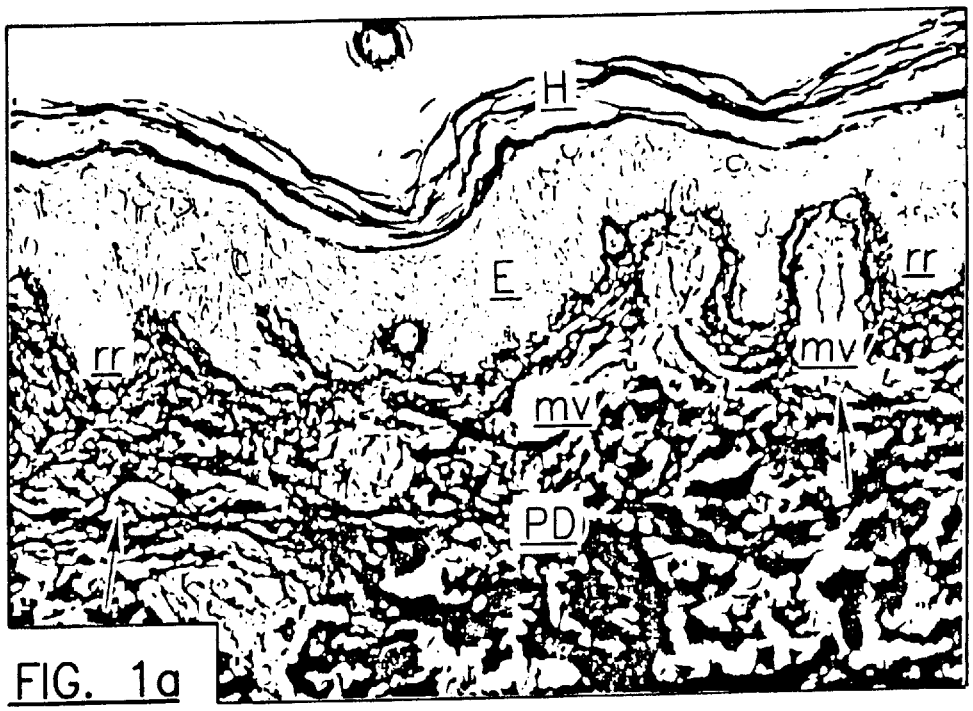
FIGS. 1*a*–1*d* are light micrographs of the epidermis and dermis of a subject treated as follows for four weeks.
Figure 1B:
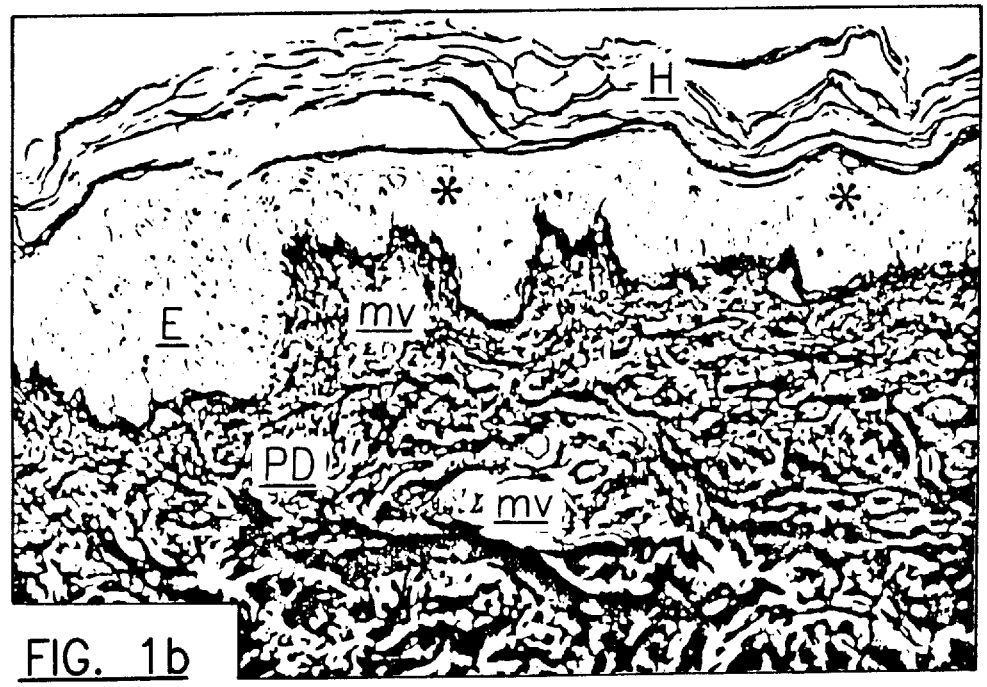
Figure 1C:
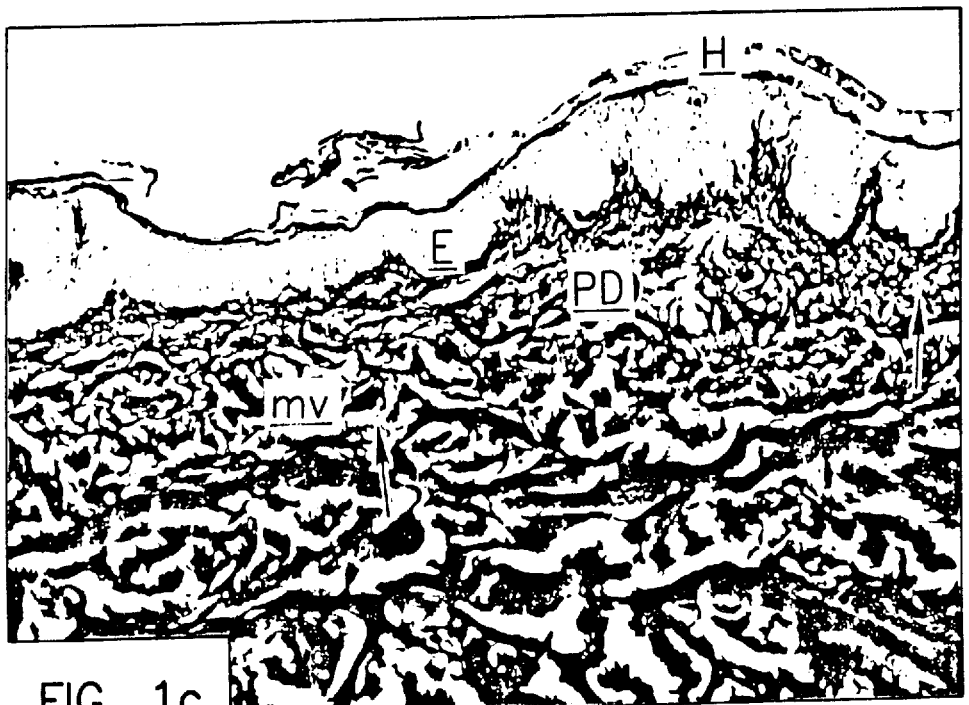
Figure 1D:
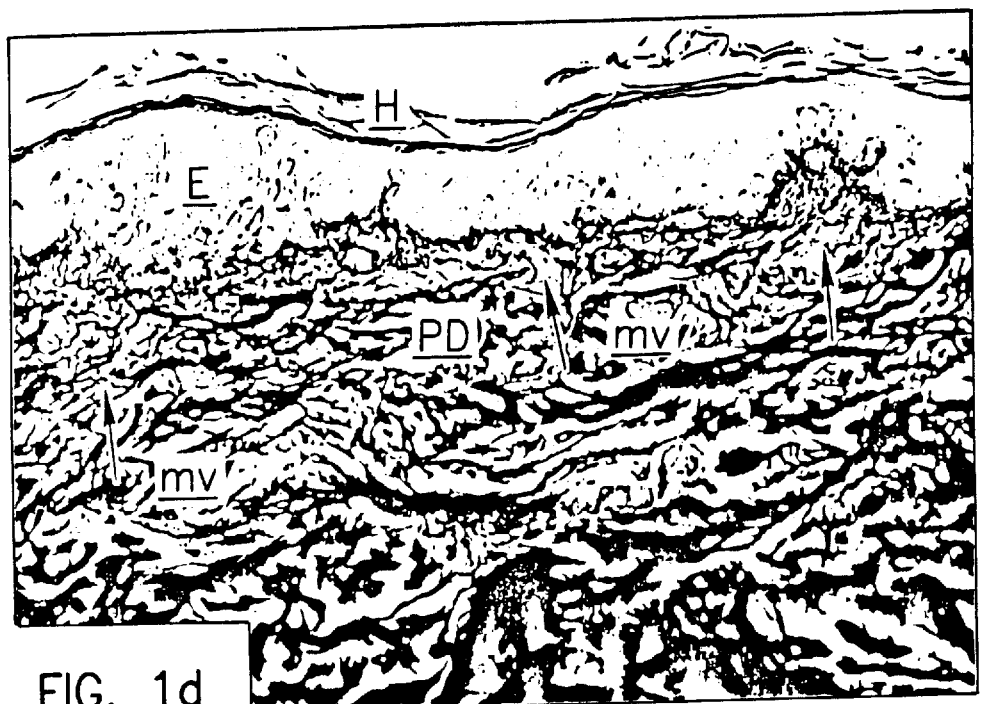

1*d*. 12% ammonium lactate following clobetasol propionate treatment.

The amount of agent applied in each of testings 1*b* through 1*d* was 0.2 ml.

The invention concerns compositions and processes for thickening skin and for lessening the atrophic effects of topical steroid usage.

Unless stated otherwise, all percentages mentioned herein are weight percentages, based on total composition weight.

All publications referred to herein are hereby incorporated by reference.

The compositions and processes of the invention employ certain salts, optional steroids and, if desired, various additives conventionally used in topical formulations.

SALTS

Useful salts are generally obtained via the reaction of suitable bases with α-hydroxyacids of formula I:

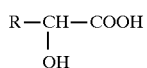

$$R-CH-COOH \quad (I)$$
$$\quad\quad |$$
$$\quad\quad OH$$

wherein R is H or a $C_{1-5}$ hydrocarbon group.

Preferably R is an alkyl group, such as a $C_{1-3}$ alkyl group, with methyl and ethyl groups being highly preferred. R is most preferably a methyl group, so that salts derived from α-hydroxypropionic acid, or lactic acid, are most preferred. Mixtures of acids may be used.

The bases used to produce the salts of the invention contain either nitrogen atoms, present as ammonium ions or amine nitrogen, or metal ions.

Ammonium-containing species to be used can be, for example, $NH_4OH$, $HN(R^1)_3OH$, or $N(R^1)_4OH$, in which each $R^1$ is independently a $C_{1-8}$ alkyl or aryl group. Mixtures are operable. Ammonium hydroxide is a preferred reactant.

Amines are another group of nitrogen-containing reactants which may be used to make the salts of the invention. Useful amines include organic primary, secondary and tertiary amines which contain 1–3 nitrogen atoms. The organic groups of these amines are generally $C_{1-8}$ alkyl or aryl groups, optionally substituted with one more hydroxyl groups. Preferred amines include alkanolamines, diamines, dialkylamines, dialkanolamines, alkylalkanolamines, trialkylamines, trialkanolamines, dialkyl- or alkanol-amines and alkyl diethanolamines.

Alternatively, the salts of the invention can be produced using metal ion-containing reagents. Preferred metal ion-containing bases are those which result in salts containing atoms of Na, K, Ca, Mg, or Li. Typically the metal ion reactants are hydroxides. Mixtures are contemplated.

The salts of the invention are produced via conventional acid/base reactions, such as that involving ammonium hydroxide and lactic acid. Conventional reaction vessels are used. Reaction temperatures to be used depend upon the particular reactants and the other reaction conditions selected.

One useful source of ammonium lactate is the 12% lotion sold as "Lac-Hydrin®" by Westwood Squibb Pharmaceutical Co.

The salts of the invention will be present, when used alone in formulations, in an amount ranging from about 1% to about 53%, preferably about 2% to about 38%.

It should be noted that, while the disclosure refers to salts of bases and α-hydroxyacids, it is contemplated that mere mixtures of these types of reagents be used. Accordingly, mixtures of acids and bases, such as those disclosed in U.S. Pat. No. 4,105,783 are also operable in the invention.

STEROIDS

The steroids useful in the invention are any of a wide variety of materials generally characterized as corticosteroids.

The steroids may be used in their base form, or they may be used as the esters, amides, ethers, etc. which are conventionally used in pharmaceutical preparations.

Steroids are generally characterized as being of high, medium, or low potency. Clobetasol propionate, a high potency steroid, has been found to be very useful in the invention. However, low and moderate potency steroids, e.g., by drocastisone and beta-methasone-17-valerate, respectively, are believed to be useful.

Among the preferred steroidal agents to be used in the invention are the corticosteroids conventionally employed in topical dermatological formulations. Thus, useful agents include those listed below:

Alclometasone dipropionate
Betamethasone
Betamethasone benzoate
Betamethasone dipropionate
Betamethasone valerate
Clobetasol propionate
Clobetasol valerate
Deprodone propionate
Desflurotriamcinolone
Dexamethasone
Dexamethasone acetate
Dexamethasone sodium phosphate
Diflorasone diacetate
Flumethasone valerate
Fluocinolone acetamide
Halobetasol propionate and others in U.S. Pat. No. 4,619,921
Hydrocortisone
Hydrocortisone acetate
Hydrocortisone valerate
Mometasone furoate
Triamcinolone acetonide Mixtures of one or more of the compounds mentioned above are operable.

In addition, the use of other conventional steroidal agents such as the free agents and other esters and amides of the agents listed above, e.g., dexamethasone valerate, whether used alone or in mixtures, are contemplated.

SALT/STEROID MIXTURES

While the salts of the invention can be topically applied separately from the steroid(s), they may also be mixed with them, i.e., in the same formulation.

When salts and steroids are used in the same formulation, the concentration of salt will be from about 1% to about 53%, preferably about 2% to about 38%. The concentration of steroid will be from about 0.0005% to about 3.0%, preferably about 0.01% to about 1.0%.

ADDITIVES

Since the formulations of the invention are to be used topically, i.e. by application to and absorption into the skin of the subject to be treated, they will usually contain certain additional ingredients which render them suitable for such use. Thus, a variety of conventional ingredients, such as emulsifiers, diluents, fillers, preservatives, moisturizers, thickeners, colorants, perfumes, buffers, etc. can be employed in these compositions in amounts of from about 0.05 to about 99.5%.

The topical formulation of the invention are generally employed as creams, lotions, ointments, gels or sprays. Other liquid or semi-solid forms are contemplated. Additives appropriate to use in these forms are also contemplated.

Other therapeutic agents may also be used in the formulations of the invention. Thus, antifungal agents (e.g., imidazoles), anesthetics (e.g., methyl solicylate), humectants (e.g., glycerin), antibacterials (e.g., erythromycin, clindamycin) and the like may be used. It should be noted that any additional therapeutic agents should be of such type(s) and in such amount(s) that their presence does not interfere with the function of the salt or the salt/steroid combination in the formulation. Generally, minor amounts of such additional therapeutic agents, i.e., about 10% or less, preferably about 0.001% to about 5%, can be used.

pH

While the pH of the systems described herein is not critical, it is generally the case that compositions whose final pH values lie between about 3.0 and about 7.5, and preferably about 4.0 and about 6.0, are operable. These pH ranges assure maximum beneficial properties for the salt in the formulations.

Depending upon the presence of a steroid or other therapeutic agent in the formulation, the use of slightly lower pH's may be beneficial.

ADMINISTRATION

Generally, the topical formulations of the invention are administered from about one to about three times, and preferably one to two times, per day.

When the salt is not applied along with the steroid, it can be applied from 4 to 24 hours, and preferably about 8 hours, before or after the administration of the steroid. It is preferred that the salt be applied after the steroid has been applied.

When the salt-containing formulation is to be used to temporarily thicken the subject's skin, the use of the formulation one to four times daily is suggested.

The individual needs of the subject and the desires of the physician may call for deviations from the routines suggested above.

The term "subject" is intended to mean any mammal upon whose skin or other dermal surface the compositions of the invention can be applied. It is generally preferred that the subject to be treated in accordance with the invention be a human patient.

Also, the salt-containing formulations of the invention can be employed to ameliorate the dermatological effects of topical steroid use for subjects of pre-adult age.

DISCUSSION OF DRAWINGS

The drawings show the sequence of epidermal and dermal changes in the same individual after treatment with nothing (a), 12% ammonium lactate (b), clobetasol propionate (c) and the combination ammonium lactate and clobetasol propionate (d) for four weeks in an open fashion.

a. Control. Normal epidermis (E) showing well developed rete ridges (rr) which results in an undulating dermal/epidermal interface. Horny layer (H) displays typical "basket weave" pattern usually associated with paraffin fixed specimens. Papillary dermis (PD) contains prominent microvasculature (mv) as well as a moderate amount of glycosaminoglycans (arrows). Magnification=200× b. 12% ammonium lactate. Viable epidermis (E) is thicker than control and shows distinct regions of blue coloration (*) indicative of the presence of glycosaminoglycans. Horny layer (H) maintains the "basket weave" pattern seen in control specimens. Papillary dermis (PD) shows a striking increase in glycosaminoglycan deposition. mv, microvasculature.

c. clobetasol propionate. Viable epidermis (E) is markedly thinner than control, and the horny layer (H) is virtually ablated. Papillary dermis (PD) appears compressed and there is a striking diminution in glycosaminoglycans (arrows) and vascular (mv) profiles.

d. combination treatment with 12% ammonium lactate and clobetasol propionate. Viable epidermis (E) appears similar in thickness to control specimens, and horny layer (H) still retains the "basket weave" appearance. Papillary dermis (PD) shows striking amounts of glycosaminoglycans (arrows) as well as numerous microvascular (mv) profiles.

In general, viable epidermis (E) is thicker and granular layer (arrows) is more prominent after ammonium lactate treatment. Note preservation of "basket weave" horny layer (H) after ammonium lactate treatment. No increase in cellularity is seen in the dermis (D) after ammonium lactate treatment. *, microvasculature ×150.

EXAMPLES

The following examples serve to illustrate the invention.

EXAMPLE I

Effects of Lac-Hydrin® on the Bioavailability of a Potent Topical Corticosteroid Experimental Design A total of 10 healthy adult volunteers between the ages of 19 and 60 years participated in this investigation. There were 5 females and 5 males.

After washing the forearms with a bland soap (Ivory®) and patting dry with a soft towel, three circular sites, each measuring 1.2 cm in diameter, were outlined in ink on the volar aspect of the forearm. Twenty microliters of each of the test products (0.05% Temovate® (clobetasol propionate) ointment, Lac-Hydrin® 12% lotion, and the combination together) were delivered to a designated test site.

On the morning of the first study date, two designated sites on each forearm received Lac-Hydrin®. The subjects returned 6–8 hours later on the same day and received Temovate® ointment to a third site and to one of the sites previously treated with Lac-Hydrin®.

One forearm was then occluded with plastic Saran Wrap® while the sites on the opposite arm were covered with circular plastic chambers in which a 1 cm hole was punched out from the center. The chambers were applied over each site and taped at the edges to prevent clothing from rubbing against or touching the skin surface. Sixteen (16) hours after the p.m. application the protective chambers and Saran Wrap® were removed and both forearms were washed again with soap and water and blotted dry with a towel.

Clinical Observations

The degree of blanching at each test site was graded 30 minutes after the products were washed from the skin, i.e., 16–17 hours after application, and again 24 hours after the last application of the test products.

Grading of the degree of blanching was done in a blind fashion using standardized lighting by the investigator who was unaware of the test product assignment and who did not participate in the application of the test products. The following grading scale was used:

0=no vasoconstriction

1=minimal visible blanching

2=definite blanching with well-defined borders

3=more intense blanching

4=intense blanching, spreading beyond the application site.

Results

The individual and total vasoconstriction scores for each test product at both time points (16 and 24 hours) are listed in Tables 1 and 2. The degree of blanching for both open and occluded applications ranged from 0–3. The mean vasoconstriction scores for both forearms were similar for both 16 and 24 hour time-points for all test sites. No blanching was observed in sites treated with Lac-Hydrin® alone. Prior treatment with Lac-Hydrin® did not appear to influence the vasoconstriction by clobetasol propionate ointment in either the open (Table 1) or occluded (Table 2) sites.

The individual scores for both forearms were compared using paired t-tests and no significant differences were found in the degree of blanching by prior treatment with Lac-Hydrin®. Thus, the treatment of the forearm with Lac-Hydrin® prior to application potent topical corticosteroid does not effect the bioavailability of the corticosteroid.

TABLE 1

BLANCHING SCORES FOR OPEN SITES

| Subject Number | Arm | Lac-Hydrin® 12% Lotion | | Lac-Hydrin® 12% Lotion & Temovate® Ointment 0.05% | | Temovate® Ointment 0.05% | |
|---|---|---|---|---|---|---|---|
| | | 16 Hrs. | 24 Hrs. | 16 Hrs. | 24 Hrs. | 16 Hrs. | 24 Hrs. |
| 1 | R | 0 | 0 | 2 | 2 | 2 | 2 |
| 2 | L | 0 | 0 | 1 | 2 | 2 | 2 |
| 3 | L | 0 | 0 | 2 | 3 | 2 | 3 |
| 4 | R | 0 | 0 | 3 | 1 | 3 | 2 |
| 5 | R | 0 | 0 | 2 | 2 | 2 | 2 |
| 6 | R | 0 | 0 | 2 | 2 | 2 | 2 |
| 7 | R | 0 | 0 | 1 | 1 | 1 | 1 |
| 8 | L | 0 | 0 | 1 | 2 | 1 | 2 |
| 9 | R | 0 | 0 | 2 | 3 | 2 | 3 |
| 10 | L | 0 | 0 | 3 | 2 | 3 | 2 |
| Total Score: | | 0 | 0 | 19 | 20 | 20 | 21 |

TABLE 2

BLANCHING SCORES FOR OCCLUDED SITES

| Subject Number | Arm | Lac-Hydrin® 12% Lotion | | Lac-Hydrin® 12% Lotion & Temovate® Ointment 0.05% | | Temovate® Ointment 0.05% | |
|---|---|---|---|---|---|---|---|
| | | 16 Hrs. | 24 Hrs. | 16 Hrs. | 24 Hrs. | 16 Hrs. | 24 Hrs. |
| 1 | L | 0 | 0 | 3 | 3 | 3 | 3 |
| 2 | R | 0 | 0 | 3 | 3 | 2 | 3 |
| 3 | R | 0 | 0 | 3 | 3 | 3 | 3 |
| 4 | L | 0 | 0 | 3 | 1 | 3 | 1 |
| 5 | L | 0 | 0 | 3 | 1 | 3 | 3 |
| 6 | L | 0 | 0 | 2 | 1 | 2 | 2 |
| 7 | L | 0 | 0 | 1 | 1 | 1 | 1 |
| 8 | R | 0 | 0 | 1 | 2 | 1 | 2 |
| 9 | L | 0 | 0 | 3 | 3 | 3 | 3 |
| 10 | R | 0 | 0 | 3 | 3 | 3 | 3 |
| Total Score: | | 0 | 0 | 25 | 21 | 24 | 24 |

EXAMPLE II

Effects of Lac-Hydrin® on Normal and Corticosteroid-Treated Human Skin

Experimental Design

Note: In this example "combination" and "salt/steroid combination" refers to the use of the salt at one time and the steroid eight hours later.

Six healthy young adult males (ages 20–34) served as volunteers. Using procedures similar to those of Example I, one site of the ventral forearm received clobetasol-17-propionate cream (0.2 ml; Temovate®, Glaxo) daily for four weeks. Another site on the ventral forearm received buffered ammonium lactate (0.2 ml; 12% Lac-Hydrin®, Westwood) daily for four weeks. A third site received a combination of Lac-Hydrin® in the morning (approximately 8:00 am) and Temovate® 8 hours later (approximately 4:00 pm), daily for four weeks. At the end of the four week treatment period, one 3 mm punch biopsy was obtained under local anesthesia from each of the treatment sites.

Untreated control biopsies were also secured at the end of four weeks.

Light Microscopy

Each 3-mm punch biopsy was fixed in 10% formalin and processed for conventional paraffin section histology.

Paraffin sections were stained with hematoxylin and eosin and Hales colloidal iron for acid mucopolysaccharides. These sections were used for histologic and histogeometric analysis.

Histometric Analysis

For estimation of epidermal thickness, care was taken to cut the sections perpendicularly to the surface. Histometric measurements of the viable epidermal area were made on both hematoxylin eosin and Hales stained sections using computer-assisted image analysis. Measurements were made from at least four sections per biopsy with each section separated by $50\mu$.

For estimation of ground substance, histometric measurements were made on Hales colloidal iron-stained sections using a Vickers M-85 microspectrophotometer.

Results

The discussion below is based on the data presented in Table 3.

Corticosteroid

All six subjects showed a marked diminution in the viable epidermis, after 4 weeks of daily treatment with Temovate®. Viable epidermal thickness decreases from an average of 66,803, to 32,476 $\mu 2$/mm of epidermis, representing a 51% decrease in thickness.

Corticosteroid+Lac-Hydrin®

All six subjects showed a diminution in viable epidermis, after 4 weeks of daily treatment with the combination, however, the magnitude was less.

Viable epidermis decreased from an average of 66,803, to 42,821 $\mu 2$/mm of epidermis, representing a 35% decrease in thickness. When compared with Temovate®, the combination of Lac-Hydrin® and Temovate® resulted in a 16% thicker viable epidermis, which was significant at the 0.05 level.

Lac-Hydrin®

Five of the six subjects showed a thickening of the viable epidermis, after 4 weeks of daily treatment with Lac- Hydrin®. One subject (#6) showed virtually no change and another subject (#5) was a weak responder. Viable epidermal thickness increased from 66,803 to 78,837 µ2/mm of epidermis, representing a 20% increase in thickness (Table 1,2). When compared with the control, this change was significant at the 0.01 level.

These findings indicate that Lac-Hydrin® has a significant sparing effect on the thinning of the viable epidermis, when used between or after applications of one of the most, if not the most, potent topical corticosteroids, i.e., clobetasol propionate.

In the study, Lac-Hydrin® alone thickened the viable epidermis significantly. This partially negates the atrophagenic effects of the steroid.

While not wishing to be bound by any particular theory of operation, applicants note that an increase in Hales stainable material in the dermis suggests that Lac-Hydrin® may stimulate fibroblasts to produce more ground substance (glycosaminoglycans). It is well known that inhibition of fibroblast synthetic activity, resulting in a decrease in ground substance, is one of the major effects of topical corticosteroids. Thus, Lac-Hydrin® may also negate the inhibitory effects of steroids on the fibroblast.

TABLE 3

CHANGE IN THICKNESS OF VIABLE EPIDERMIS TREATMENT WITH STEROID, SALT AND SALT/STEROID COMBINATION

| | EPIDERMAL THICKNESS* | | | | % CHANGE | | |
|---|---|---|---|---|---|---|---|
| Subject | Control | Steroid | Salt/ Steroid | Salt | Steroid | Salt/ Steroid | Salt |
| 1 | 58496 | 25770 | 35535 | 80503 | −56 | −39 | 38 |
| 2 | 62506 | 29345 | 39532 | 93657 | −53 | −37 | 50 |
| 3 | 69735 | 31814 | 41397 | 77813 | −54 | −41 | 12 |
| 4 | 73033 | 46750 | 57427 | 82743 | −36 | −21 | 13 |
| 5 | 83400 | 34477 | 42700 | 84834 | −58 | −48 | 2 |
| 6 | 53645 | 26705 | 40337 | 53469 | −50 | −25 | 0 |

*Values are sq. microns/mm of epidermis
**Values represent the delta percent calculations. Negative values indicate percentage decreases; positive values indicate percentage increases.

EXAMPLE III

Study of the Effect of Ammonium Lactate on Effectiveness of Steroid treatment of Rhus Dermatitis (Poison Ivy)

This is a study of topical anti-inflammatory activity conducted in 12 healthy volunteer subjects of both sexes. All 12 were enrolled after they had developed reactions in four sites to topically applied Rhus extract antigen. The four test sites (2 on each forearm) were treated daily with measured amounts (~20 uL) of the following (1) Lac-Hydrin® 12% lotion; (2) Temovate® (clobetasol propionate) 0.05% cream; (3) the combination of Temovate® and Lac-Hydrin®, applied in the a.m. and the p.m., respectively, and (4) Petrolatum U.S.P. (control). After applying the treatments to designated sites, the sites were covered with band-aids. Treatments were applied once daily for 5 consecutive days (Monday to Friday) and the sites evaluated visually for edema, erythema, vesiculation etc. on Friday p.m. by a dermatologist.

Efficacy is measured by the degree of resolution of the dermatitis compared to a treated control site.

Test Materials

The test materials were supplied by the investigator and were labelled alphabetically as A, B or C. The four test sites were assigned either treatment A, treatment B, A+B (or B+A) and Treatment C. The treatment codes were as follows:

A=Lac-Hydrin® (ammonium lactate) 12% lotion; lot #57B161 (Expiration 10/92) Westwood Pharmaceuticals, Inc., Buffalo, N.Y. 14213 (USA) applied at a.m. visit B=Temovate® (clobetasol propionate) cream 0.05% lot #Z7740DA (Expiration 05/92) Glaxo Dermatology Products, Glaxo, Inc., Research Triangle Park, N.C. 27709 (USA) applied at p.m. visit A+B=Lac Hydrin® 12% lotion applied at a.m. visit and Temovate® cream 0.05% applied at p.m. visit B+A=Temovate® cream 0.05% applied at a.m. visit and Lac-Hydrin® 12% lotion applied at p.m. visit C=Vaseline® white petrolatum, USP, lot #938-C Chesebrough-Pond's, Inc., Greenwich, Conn. 06830 (USA) applied at a.m. visit Study Group Rhus-antigen extract (Hollister-Stier Laboratories) was applied as described below to designated sites on both forearms to 19 volunteers with a strong positive history of poison-ivy dermatitis. Of these, 12 developed an acute vesicular dermatitis of equal intensity in all four sites. In the remaining 7, the reactions were either too weak or unequal in intensity and they were dropped from the study. The 12 subjects with equal responses were then allowed to remain in the study and received the treatment schedules as outlined below.

Procedure

After washing the forearms with a bland soap (Ivory) and patting dry with a soft towel, four circular sites were outlined (two on the volar aspect of each forearm) with ink. The dermatitis was induced by the application of 10 microliters of 1:50 dilution of poison oak-poison ivy oleoresin (Hollister-Stier Laboratories) to a 0.6cm disc of filter paper. The filter paper disc was then applied to the skin and taped with impermeable plastic tape (Blenderm, 3M®). The Blenderm was further secured with a non-woven surgical tape (Scanpor). This patch was left in place for six (6) hours. At the end of six hours, the patch was removed and the area washed with soap and water and then dried.

The induction patches were applied on Friday, Nov. 9, 1990. The volunteers returned to the laboratory on Monday, November 12 in the morning, at which time the test sites were examined and graded. Only individuals with equal responses (dermatitis) in all four sites were allowed to continue in the study.

Treatment Plan

Each site received about 20 uL of A, B, A+B or C as described under "materials". Test product applications were randomized according to a randomization schedule prepared by the investigator (Appendix B). The test products were gently rubbed into the sites using clean glass rods and the sites were then covered by a band-aid to prevent rubbing against clothing, etc. In six volunteers (#1, #2, #3, #4, #5 and #11), Lac-Hydrin® was applied first (in the a.m.) followed by Temovate® in the p.m., while in the remaining six volunteers, (#6, #7, #8, #9, #10 and #12) the sequence of applications were reversed viz. Temovate® was applied in the a.m. and Lac-Hydrin® in the p.m. The remaining three test sites received either Lac-Hydrin® alone (A) in the a.m., Temovate® alone in the p.m. or Vaseline in the a.m.

Treatments were continued for 5 consecutive days. On the last day, the sites were visually graded by the investigator who was unaware of product assignment and who did not participate in product application or treatment. The forearms were also photographed after they were graded.

Grading Scale

The following scale was used to grade all Rhus-induced dermatitis:

0=complete clearing

1=minimally elevated or palpable border with faint erythema

2=more elevated lesion with diffuse edema or palpable infiltration and moderate erythema 3=uniformly raised lesions with intense edema, erythema and scaling or crusting 4=marked edema, intense erythema and vesiculation Adverse Reactions Patients were instructed by the investigator to report immediately the occurrence of any adverse experience. The adverse reaction(s), if any, were recorded and described in detail (nature and intensity). Dates of occurrence of any such reaction were noted, along with dates of the details concerning any necessary discontinuation or interruption of therapy. Any adverse reaction would have been reported immediately to the sponsor by telephone and in writing within five days.

Results

Of the 19 original volunteers, only the 12 volunteers listed in Table 1 qualified for continuation in the study and completed the investigation as outlined. There were no adverse reactions or unexpected side-effects of any kind.

The reaction scores recorded at the outset of the study before treatments were started are listed in Table 4. The mean score (±S.D.) for each test site was 3.4+0.5. The scores recorded on the last day of treatment are displayed in Table 5.

TABLE 4

GRADES - DAY 0, by Treatment

| Subject Number | Lac-Hydrin® 12% Lotion | Temovate® Cream 0.05% | Lac-hydrin & Temovate | Vaseline® White Petrolatum (U.S.P.) |
| --- | --- | --- | --- | --- |
| 01 | 4 | 4 | 4 | 4 |
| 02 | 3 | 3 | 3 | 3 |
| 03 | 4 | 4 | 4 | 4 |
| 04 | 3 | 3 | 3 | 3 |
| 05 | 3 | 3 | 3 | 3 |
| 06 | 4 | 4 | 4 | 4 |
| 07 | 4 | 4 | 4 | 4 |
| 08 | 3 | 3 | 3 | 3 |
| 09 | 3 | 3 | 3 | 3 |
| 10 | 3 | 3 | 3 | 3 |
| 11 | 4 | 4 | 4 | 4 |
| 12 | 3 | 3 | 3 | 3 |
| Mean (X) ± | 3.4 | 3.4 | 3.4 | 3.4 |
| S.D. | 0.5 | 0.5 | 0.5 | 0.5 |

TABLE 5

GRADES - DAY 4, by Treatment

| Subject Number | Lac-Hydrin® 12% Lotion | Temovate® Cream 0.5% | Lac-hydrin® & Temovate® | Vaseline® White Petrolatum (U.S.P.) |
| --- | --- | --- | --- | --- |
| 01 | 4 | 2 | 2 | 4 |
| 02 | 3 | 1 | 1 | 3 |
| 03 | 4 | 2 | 1 | 4 |
| 04 | 3 | 1 | 1 | 3 |
| 05 | 1 | 1 | 1 | 2 |
| 06 | 2 | 0 | 0 | 2 |
| 07 | 4 | 3 | 2 | 4 |
| 08 | 3 | 1 | 1 | 3 |
| 09 | 2 | 0 | 0 | 2 |
| 10 | 3 | 2 | 2 | 3 |
| 11 | 4 | 1 | 1 | 4 |
| 12 | 1 | 1 | 2 | 1 |
| Mean (X) ± | 2.8 | 1.3 | 1.2 | 2.9 |
| S.D. | 1.1 | 0.9 | 0.7 | 1.0 |

There was no major difference in the mean reaction score following treatment by Lac-Hydrin® compared to petrolatum U.S.P. (mean scores of 2.8 and 2.9 respectively). Nor were there any discernable differences between sites treated with Temovate® and with Temovate® plus Lac-Hydrin®, regardless of the sequence or order of application.

The results confirmed that Lac-Hydrin® had no noticeable effect above that of Petrolatum and did not influence the anti-inflammatory activity of Temovate®.

Temovate® alone or with Lac-Hydrin® produced a highly significant (P=0.0001) effect in terms of enhancing the resolution of the dermatitis compared to treatment with petrolatum alone or Lac-Hydrin® alone.

DISCUSSION

There is little doubt that the use of Lac-Hydrin® after the use of corticosteroids results in a sparing of the viable epidermis. Examples I and III indicates that this sparing effect was not due to either dilution of the steroid or diminution of its efficacy.

The data generated for Lac-Hydrin® on normal skin (Example II) suggests that this product may behave like a retinoid with respect to changes in the morphology of the epidermis and dermis (thickens the epidermis, increases ground substance). While the Lac-Hydrin® effects do not appear to be as profound as those of the retinoids, significant changes are achieved without any clinical signs of irritation. This is a major advantage over retinoid therapy for such conditions as aging skin.

It is contemplated, then, that long-term use of topical Lac-Hydrin® could reverse some of the changes that normally occur to aged skin (thinning of the epidermis and dermis), with much less irritation than is generally caused by retinoids.

Reasonable variations, such as those which would occur to a skilled artisan, can be made herein without departing from the scope of the invention.

What is claimed is:

1. A method for decreasing the reduction of the thickness of viable epidermis of mammalian skin contacted with a steroid in an amount that causes said reduction comprising contacting said skin with a viable epidermis thickness increasing amount of a dermatologically acceptable salt of an alpha-hydroxy acid of the formula:

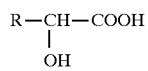

wherein R is hydrogen or a $C_{1-5}$ hydrocarbon group, said decrease in the reduction of the thickness of the viable epidermis being in comparison to skin contacted with said amount of said steroid but not contacted with said dermatologically acceptable salt of an alpha-hydroxy acid.

2. The method of claim 1, wherein the salt is a reaction product of said alpha-hydroxy acid and a metal ion containing base or a base containing a nitrogen atom present in an ammonium ion or an amine.

3. The method of claim 1, wherein the steroid is in a dermatologically acceptable composition containing from about 0.005 wt % to about 3 wt % steroid.

4. The method of claim 1, wherein said skin is contacted with the steroid and the α-hydroxy acid salt simultaneously.

5. The method of claim 2, wherein said skin is contacted with the steroid and the α-hydroxy acid salt simultaneously.

6. The method of claim 3, wherein said skin is contacted with the steroid and the α-hydroxy acid salt simultaneously.

7. The method of claim 1, wherein said skin is contacted with the steroid and the α-hydroxy acid salt sequentially.

8. The method of claim 2, wherein said skin is contacted with the steroid and the α-hydroxy acid salt sequentially.

9. The method of claim 3, wherein said skin is contacted with the steroid and the α-hydroxy acid salt sequentially.

10. The method of claim 5, wherein said skin is contacted with the α-hydroxy acid salt at a time period up to eight hours after said contacting with steroid.

11. A method for decreasing skin atrophy of mammalian skin contacted with a steroid in an amount that causes skin atrophy comprising contacting said skin with a skin atrophy decreasing amount of a dermatologically acceptable salt of an alpha-hydroxy acid of the formula:

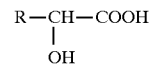

wherein R is hydrogen or a $C_{1-5}$ hydrocarbon group, said decrease in the reduction of skin atrophy being in comparison to skin contacted with said amount of said steroid but not contacted with said dermatologically acceptable salt of an alpha-hydroxy acid.

12. The method of claim 11, wherein the salt is a reaction product of said alpha-hydroxy acid and a metal ion containing base or a base containing a nitrogen atom present in an ammonium ion or an amine.

13. The method of claim 11, wherein the steroid is in a dermatologically acceptable composition containing from about 0.005 wt % to about 3 wt % steroid.

14. The method of claim 11, wherein the steroid and the α-hydroxy acid salt are applied simultaneously.

15. The method of claim 12, wherein the steroid and the α-hydroxy acid salt are applied simultaneously.

16. The method of claim 12, wherein the steroid and the α-hydroxy acid salt are applied simultaneously.

17. The method of claim 11, wherein the steroid and the α-hydroxy acid salt are applied sequentially.

18. The method of claim 12, wherein the steroid and the α-hydroxy acid salt are applied sequentially.

19. The method of claim 13, wherein the steroid and the α-hydroxy acid salt are applied sequentially.

20. The method of claim 11, wherein the α-hydroxy acid salt is applied to the skin at a time period up to eight hours after said contacting with steroid.

* * * * *